US008927027B2

(12) United States Patent
Fournell et al.

(10) Patent No.: US 8,927,027 B2
(45) Date of Patent: Jan. 6, 2015

(54) HUMAN MILK PERMEATE COMPOSITIONS AND METHODS OF MAKING AND USING SAME

(75) Inventors: Joseph Fournell, Newbury Park, CA (US); Scott Eaker, Thousand Oaks, CA (US); Scott Elster, Glendale, CA (US); David J. Rechtman, Hermosa Beach, CA (US)

(73) Assignee: Prolacta Bioscience, City of Industry, CA (US)

( * ) Notice: Subject to any disclaimer, the term of this patent is extended or adjusted under 35 U.S.C. 154(b) by 0 days.

(21) Appl. No.: 13/132,545

(22) PCT Filed: Dec. 2, 2009

(86) PCT No.: PCT/US2009/066430
§ 371 (c)(1),
(2), (4) Date: Jul. 7, 2011

(87) PCT Pub. No.: WO2010/065652
PCT Pub. Date: Jun. 10, 2010

(65) Prior Publication Data
US 2011/0256233 A1 Oct. 20, 2011

Related U.S. Application Data (60) Provisional application No. 61/119,176, filed on Dec. 2, 2008, provisional application No. 61/193,546, filed on Dec. 5, 2008.

(51) Int. Cl.
| | | |
|---|---|---|
| A61K 35/20 | (2006.01) | |
| A61K 35/12 | (2006.01) | |
| A23C 9/148 | (2006.01) | |
| A23C 9/20 | (2006.01) | |
| A23L 1/29 | (2006.01) | |
| A23C 9/142 | (2006.01) | |

(52) U.S. Cl.
CPC ............. *A61K 35/20* (2013.01); *A23V 2002/00* (2013.01); *A23C 9/148* (2013.01); *A23C 9/206* (2013.01); *A23L 1/296* (2013.01); *A23C 9/1422* (2013.01)
USPC .......................................... 424/535; 424/520

(58) Field of Classification Search
USPC ................................................. 424/535, 520
See application file for complete search history.

(56) References Cited

U.S. PATENT DOCUMENTS

| | | | |
|---|---|---|---|
| 2,567,898 A | 9/1951 | Staaff | |
| 3,946,113 A | 3/1976 | Seiberling | |
| 4,362,697 A | 12/1982 | Tabb et al. | |
| 4,455,483 A | 6/1984 | Schonhuber | |
| 4,762,822 A | 8/1988 | Ettinger | |
| 4,772,262 A | 9/1988 | Grant et al. | |
| 4,876,100 A | 10/1989 | Holm et al. | |
| 4,948,599 A | 8/1990 | Sagara et al. | |
| 5,064,674 A | 11/1991 | Girsh | |
| 5,169,766 A | 12/1992 | Schuster et al. | |
| 5,256,437 A | 10/1993 | Degen et al. | |
| 5,303,598 A | 4/1994 | Binder et al. | |
| 5,334,822 A | 8/1994 | Sanford | |
| 5,401,523 A | 3/1995 | Degen et al. | |
| 5,505,955 A | 4/1996 | Peterson et al. | |
| 5,541,065 A | 7/1996 | Erlich et al. | |
| 5,576,040 A | 11/1996 | Moller et al. | |
| 5,605,689 A | 2/1997 | Ammann | |
| 5,616,483 A | 4/1997 | Bjursell et al. | |
| 5,670,196 A | 9/1997 | Gregory | |
| 5,683,733 A | 11/1997 | Krabsen et al. | |
| 5,707,678 A | 1/1998 | Gregory | |
| 5,972,337 A | 10/1999 | Ceriani et al. | |
| 5,983,198 A | 11/1999 | Mowery et al. | |
| 6,004,288 A | 12/1999 | Hochstedler et al. | |
| 6,017,511 A | 1/2000 | Wong et al. | |
| 6,020,015 A | 2/2000 | Gaull | |
| 6,056,978 A | 5/2000 | Beck et al. | |
| 6,183,803 B1 | 2/2001 | Morcol et al. | |
| 6,194,009 B1 | 2/2001 | Kamarel | |
| 6,270,827 B1 | 8/2001 | Gaull et al. | |
| 6,294,206 B1 | 9/2001 | Barrett-Reis et al. | |
| 6,613,367 B1 | 9/2003 | Wells et al. | |
| 6,635,296 B1 | 10/2003 | Nissen et al. | |
| 6,652,900 B2 | 11/2003 | Lindquist | |
| 6,670,124 B1 | 12/2003 | Chow et al. | |
| 6,737,096 B2 | 5/2004 | Lindquist | |
| 6,780,987 B1 | 8/2004 | Herman et al. | |
| 6,846,298 B1 | 1/2005 | Carr et al. | |
| 6,910,594 B2 | 6/2005 | Foley et al. | |
| 7,829,130 B2 * | 11/2010 | Tossavainen et al. | ......... 426/580 |
| 7,867,541 B2 | 1/2011 | McMahon et al. | |
| 7,914,822 B2 | 3/2011 | Medo | |

(Continued)

FOREIGN PATENT DOCUMENTS

| | | |
|---|---|---|
| EP | 1637043 A1 | 3/2006 |
| GB | 1451747 A | 10/1976 |

(Continued)

OTHER PUBLICATIONS

German et al. (Human Milk Oligosaccharides: Evolution, Structures and Bioselectivity as Substrates for Intestinal Bacteria. Nestle Nutr Workshop Ser Pediatr Program (2002): (62):205-222).*

(Continued)

*Primary Examiner* — Karen Cochrane Carlson
*Assistant Examiner* — Natalie Moss
(74) *Attorney, Agent, or Firm* — Cooley LLP (57) ABSTRACT

This disclosure features human milk permeates and compositions containing the same obtained from fractionated whole human milk. The oligosaccharide rich permeate and permeate compositions of the present invention are useful as nutritional supplements for pre-term and full term infants, for establishing or maintaining gut flora and for treating the symptoms of inflammatory bowel disease.

4 Claims, 7 Drawing Sheets

(56) References Cited

U.S. PATENT DOCUMENTS

| | | | |
|---|---|---|---|
| 7,943,315 B2 | 5/2011 | Medo et al. | |
| 7,951,410 B2 | 5/2011 | McMahon et al. | |
| 8,278,046 B2 | 10/2012 | Medo et al. | |
| 2001/0034614 A1 | 10/2001 | Fletcher-Haynes et al. | |
| 2001/0049096 A1 | 12/2001 | Brown | |
| 2002/0155445 A1 | 10/2002 | Jarvik | |
| 2002/0182243 A1 | 12/2002 | Medo | |
| 2003/0093171 A1 | 5/2003 | Soehnlen | |
| 2003/0152942 A1 | 8/2003 | Fors et al. | |
| 2003/0175701 A1 | 9/2003 | Griffiths et al. | |
| 2003/0219812 A1 | 11/2003 | Quay et al. | |
| 2004/0181205 A1 | 9/2004 | Morton et al. | |
| 2004/0265462 A1 | 12/2004 | Carlson | |
| 2005/0053707 A1 | 3/2005 | Kopf et al. | |
| 2005/0096295 A1 | 5/2005 | McMahon et al. | |
| 2005/0100634 A1 | 5/2005 | Medo | |
| 2005/0214358 A1 | 9/2005 | Mikoshiba et al. | |
| 2005/0220894 A1 | 10/2005 | Williams et al. | |
| 2006/0115558 A1 | 6/2006 | Lamothe | |
| 2006/0204632 A1 | 9/2006 | Barrett-Reis et al. | |
| 2006/0233915 A1 | 10/2006 | Puski et al. | |
| 2007/0098863 A1 | 5/2007 | Medo et al. | |
| 2007/0104700 A1 | 5/2007 | Garcia-Rodenas et al. | |
| 2007/0203802 A1 | 8/2007 | Medo et al. | |
| 2008/0118615 A1 | 5/2008 | Hartmann et al. | |
| 2008/0124430 A1 | 5/2008 | Medo et al. | |
| 2008/0187619 A1 | 8/2008 | Hartmann et al. | |
| 2008/0227101 A1 | 9/2008 | Medo et al. | |
| 2008/0254165 A1 | 10/2008 | Patel et al. | |
| 2008/0274230 A1 | 11/2008 | Johns et al. | |
| 2009/0181848 A1 | 7/2009 | Lenz et al. | |
| 2009/0203592 A1 | 8/2009 | Beermann et al. | |
| 2009/0258121 A1 | 10/2009 | Medo | |
| 2010/0268658 A1 | 10/2010 | Medo et al. | |
| 2010/0280115 A1 | 11/2010 | Medo et al. | |
| 2011/0206684 A1 | 8/2011 | Medo | |
| 2011/0256269 A1* | 10/2011 | Medo et al. | 426/72 |
| 2011/0311689 A1 | 12/2011 | Medo et al. | |

FOREIGN PATENT DOCUMENTS

| | | |
|---|---|---|
| JP | 61-33895 U | 1/1986 |
| JP | 64-67141 A | 3/1989 |
| JP | 6-303900 A | 11/1994 |
| JP | 2001-517949 | 10/2001 |
| JP | 2002-532074 A | 10/2002 |
| JP | 2002-540806 A | 12/2002 |
| JP | 2003-047402 | 2/2003 |
| JP | 2003-113087 | 4/2003 |
| JP | 2005-525116 A | 8/2005 |
| JP | 2008-512398 | 4/2008 |
| SE | 380422 B | 11/1975 |
| WO | WO 9857549 | 12/1998 |
| WO | WO 00/43550 A2 | 7/2000 |
| WO | WO 2005/013709 A1 | 2/2005 |
| WO | WO 2005/051088 A2 | 6/2005 |
| WO | WO 2005/084129 A2 | 9/2005 |
| WO | WO 2006/026878 A1 | 3/2006 |
| WO | WO 2006/026879 A1 | 3/2006 |
| WO | WO 2007/035870 A2 | 3/2007 |
| WO | WO 2007/051475 | 5/2007 |
| WO | WO 2008/027572 A1 | 3/2008 |
| WO | WO 2008/067486 A2 | 6/2008 |
| WO | WO 2008/073888 A2 | 6/2008 |
| WO | WO 2010/030764 A2 | 3/2010 |

OTHER PUBLICATIONS

"International Search Report," 2 pages, PCT appl. No. PCT/US2012/049590 (mailed Oct. 1, 2012).
"Written Opinion of the International Searching Authority," 6 pages, PCT appl. No. PCT/US2012/049590 (mailed Oct. 1, 2012).
Cowan et al., "Milk permeate as a dietary supplement for lactating dairy cows," Aus. J. Exp. Agric. 30(6):807-810 (1990).
Geilman et al., "Production of an electrolyte beverage from milk permeate," J. Dairy Sci. 75(9):2364-2369 (1992).
Luck and Nau, "Nicotine and cotinine concentrations in the milk of smoking mothers: influence of cigarete consumption and diurnal variation," Eur J. Pediatr. 146:21-26 (1987).
Supplementary European Search Report mailed Oct. 29, 2012 in co-pending European application No. EP 09831061.8, 5 pages.
Arnold, "How North American Donor Banks Operate: Results of a Survey: Part 1," J. Hum. Lact. 13(2):159-162 (1997).
Arnold, "How North American Donor Banks Operate: Results of a Survey: Part 2," J. Hum. Lact. 13(3):243-246 (Sep. 1997).
Arnold, "How to Order Banked Donor Milk in the United States: What the Health Care Provider Needs to Know," J. Hum. Lact. 14(1):65-67 (1998).
Bernshaw, "Milk Banking: An Idea That Has Come of Age. Non-Profit Milk Banking," Seminar delivered on Aug. 29, 2006. Retrieved from the internet: http://www.utahbreastfeeding.org/business/2006_08_MilkBankNotes.pdf.
Boehm, G., et al., "Metabolic Differences Between AGA- and SGA-Infants of Very Low Birthweight II Relationship to Protein Intake," Acta Pædiatrica Scandinavica, Almqvist, Och Wiksell, Stockholm, SE, vol. 77, No. 5, Jan. 1, 1988, pp. 642-646.
Burger and Schumm, "Detection of a Minor contributor in a DNA Sample Mixture from Human Milk," International Congress Series 1288:547-549 (2006).
Burger et al., "Detection of a 1% to 2% Contributor in a DNA Sample Mixture From Human Milk," International Society for Forensic Genetics $21^{st}$ Congress Conference Programme and Abstracts [online], Sep. 12-17, 2005 [retrieved on Mar. 26, 2007]. Retrieved from the Internet: http://www.ipatimup.pt/isfg2005/PROGRAMME.pdf; p. 75.
Carey et al., "Growth and phosphorus metabolism in premature infants fed human milk, fortified human milk, or special premature formula. Use of serum procollagen as a marker of growth," Am. J. Dis. Children 141(5):511-515 (1987).
Casey, "The nutritive and metabolic advantages of homologous milk," Proc. Nutr. Soc. 48:271-281 (1989).
Davies, D. P., "Adequacy of Expressed Breast Milk for Early Growth of Preterm Infants," Arch. Disease in Childhood. 1977. vol. 52, pp. 296-301.
Friis and Andersen, "Rate of inactivation of cytomegalovirus in raw banked milk during storage at -20° C. and pasteurisation," Br. Med. J. 285:1604-1605 (1982).
Fukushima et al., "Consumption of cow milk and egg by lactating women and the presence of β-lactoglobulin and ovalbumin in breast milk," Am. J. Clin. Nutr. 65:30-35 (1997).
Gartner et al., "Breastfeeding and the use of human milk," Pediatr. 115(2):496-506 (2005).
Hagelberg S., et al., "Amino Acid Levels in the Critically Ill Preterm Infant Given Mother's Milk Fortified with Protein from Human or Cow's Milk" Acta Paediatr. Scand.1990. vol. 79, pp. 1163-1174.
Hagelberg, S., et al., "The Protein Tolerance of Very Low Birth Weight Infants Fed Human Milk Protein Enriched Mothers' Milk" Acta Paediatr. Scand. 1982. vol. 71, pp. 597-601.
Hartmann et al., "Best Practice Guidelines for the Operation of a Donor Human Milk Bank in an Australian NICU," Early Human Devel. 83:667-673 (2007).
Hylmö, P., et al., "Preparation of Fat and Protein from Banked Human Milk: Its Use in Feeding Very-Low-Birth-Weight Infants," Human Milk Banking, edited by A.F. Williams and J.D. Baum, Nestle Nutrition, Vewey/Raven Press, New York, 1984, pp. 55-61.
Itabashi et al., "Fortified preterm human milk for very low birth weight infants," Early Hum. Devel. 29:339-343 (1992).
Jenness and Palmer, "Substances Adsorbed on the Fat Globules in Cream and Their Relation to Churning. V. Composition of the 'Membrane' and Distribution of the Adsorbed Substances in Churning," J. Dairy Science 28(8):611-623 (1945).
Jensen et al., "Lipids in Human Milk and Infant Formulas," Ann. Rev. Nutr. 12:417-441 (1992).
Jensen et al., "Lipids of Bovine and Human Milks: A Comparison," J. Dairy Science 73:223-240 (1990).
Klein, Catherine J., "Nutrient Requirements for Preterm Infant Formulas," J. Nutr. 132:1395S-1577S, 1577S, 2002.

(56) References Cited

OTHER PUBLICATIONS

Krukovsky et al., "The Effects of Nordihydroguaiaretic Acid, Salt, and Temperature of Storage on the Stability of Fat and Fat-Soluble Vitamins in Cream and Butter," J. Dairy Science 32(7):679-687 (1949).
Lawrence, "Storage of human milk and the influence of procedures on immunological components of human milk," Acta Pædiatr. 88:14-18 (1999).
Lindblad B.S., et al., "Blood Levels of Critical Amino Acids in Very Low Birthweight Infants on a High Human Milk Protein Intake" Acta Paediatr. Scand.1982.vol. 296, pp. 24-27.
Lönnerdal, "Biochemistry and physiological function of human milk proteins," Am. J. Clin. Nutr. 42:1299-1317 (1985).
Lucas et al., "A human milk formula," Early Hum. Devel. 4/1:15-21 (1980).
McKiernan and Hull, "The Constituents of Neonatal Milk," Pediatr. Res. 16:60-64 (1982).
Moro et al., "Fortification of Human Milk: Evaluation of a Novel Fortification Scheme and of a New Fortifier," J. Ped. Gastroenterol. Nutr. 20:162-172 (1995).
Moro, G.E., et al., "Growth and Metabolic Responses in Low-Birth-Weight Infants Fed Human Milk Fortified with Human Milk Protein or with a Bovine Milk Protein Preparation," J. Pediatric Gastroenterol. and Nutr. 1991. vol. 13, pp. 150-154.
Ogundele,"Techniques for the storage of human breast milk: implications for anti-microbial functions and safety of stored milk," Eur. J. Pediatr. 159:793-797 (2000).
Panzer et al., "Immune thrombocytopenia in severe hemophilia A treated with high-dose intravenous immunoglobulin," Transfusion 26:69-72 (1986).
Polberger, S.K.T., "Fortified Human Milk for Very Low Birth Weight Infants: Effects on Growth and Metabolism," Dept. Pediatrics, University of Lund, Malmo 1990, pp. 1-148.
Polberger, S.K.T., et al., "Amino Acid Concentrations in Plasma and Urine in Very Low Birth Weight Infants Fed Non-Protein-Enriched or Human Milk Protein-Enriched Human Milk," Department of Pediatrics, University of Lund, Malmö General Hospital, S-21401 Malmö Sweden, pp. 131-148. Pediatrics 1990; 86: 909-915.
Polberger, S.K.T., et al., "Assessment of Eleven Different Plasma Proteins as Indicators of Protein Nutritional Status in Very Low Birth Weight Infants," Department of Pediatrics, University of Lund, Malmö General Hospital, S-21401 Malmö Sweden, 1990, pp. 115-129.
Polberger, S.K.T., et al., "Concentrations of Twelve Plasma Proteins at Birth in Very Low Birth Weight and in Term Infants," Department of Pediatrics, University of Lund, Malmö General Hospital, S-21401 Malmö Sweden, pp. 101-114. Acta Paediatr Scand. 1990; 79(8-9): 729-736.
Polberger, S.K.T., et al., "Growth of Very Low Birth Weight Infants on Varying Amounts of Human Milk Protein," Department of Pediatrics, University of Lund, Malmö General Hospital, S-21401 Malmö Sweden, pp. 69-87. Pediatr Res 1989; 25: 414-419.
Polberger, S.K.T., et al., "Urinary and Serum Urea as Indicators of Protein Metabolism in Very Low Birth Weight Infants Fed Varying Human Milk Protein Intakes," Department of Pediatrics, University of Lund, Malmö General Hospital, S-21401 Malmö Sweden, pp. 89-99. Acta Paediatr Scand. 1990; 79(8-9): 737-742.
Prentice, "Constituents of Human Milk," *Food and Nutrition Bulletin*, the United Nations University Press, 17(4), Dec. 1996. Retrieved from the Internet: http://www.inffoundation.org/FNB/FNBIndexNEW.html.
Rönnholm, K., et al., "Supplementation with Human Milk Protein Improves Growth of Small Premature Infants Fed Human Milk," Pediatrics. 1986. vol. 77, No. 5, pp. 649-653.
Rönnholm, Kar., et al., "Human Milk Protein and Medium-Chain Triglyceride Oil Supplementation of Human Milk: Plasma Amino Acids in Very Low-Birth-Weight Infants," Pediatrics, American Academy of Pediatrics, Evanston, IL, vol. 74, No. 5, Jan. 1, 1984, pp. 792-799.
Saiki et al., "Genetic analysis of amplified DNA with immobilized sequence-specific oligonucleotide probes," Proc. Natl. Acad. Sci. USA 86:6230-6234 (1989).
Schanler et al., "Feeding strategies for premature infants: beneficial outcomes of feeding fortified human milk versus preterm formula," Pediatr. 103(6 Pt 1):1150-1157 (1999).
Schanler, R., et al., "Enhanced Fecal Excretion of Seleted Immune Factors in Very Low Birth Weight Infants Fed Fortified Human Milk," Pediatric Research. 1986. vol. 20, No. 8, pp. 711-715.
Schanler, R., et al., "Fortified mothers' milk for very low birth weight infants; results of growth and nutrient balance studies," J. Pediatrics. 1985. vol. 107, No. 3, pp. 437-444.
Schanler, R., et al., "Fortified mothers' milk for very low birth'weight infants: results in macromineral balance studies," J. Pediatrics. 1985. vol. 107, No. 5, pp. 767-774.
Schanler, R., et al., "Mineral balance studies in very low birth weight infants fed human milk," J. Pediatrics. 1988. vol. 113, vol. 1, Part 2, pp. 230-238.
Srinivasan, L., et al., "Increased osmolality of breast milk with therapeutic additives," Arch. Dis. Child. Fetal. Neonatal Ed. 2004. 89:F514-F517.
Supplementary European Search Report mailed Apr. 20, 2011 in co-pending European application No. EP 07811645.6, 7 pages.
Supplementary European Search Report mailed Apr. 27, 2011 in co-pending European application No. EP 07864921.7, 8 pages.
Supplementary European Search Report mailed Mar. 24, 2009 in co-pending European application No. EP 06815100.0, 6 pages.
Supplementary European Search Report mailed Oct. 15, 2010 in co-pending European application No. EP 07865463.9, 6 pages.
Terpstra, et al., "Antimicrobial and Antiviral Effect of High-Temperature Short-Time (HTST) Pasteurization Applied to Human Milk," Breastfeeding Med. 2007. vol. 2, pp. 27-33.
The Dairy Council, "The Nutritional Composition of Dairy Products," pp. 1-49, 2002.
Tully, "Is Pasteurized Mother's Own or Donor Milk an Answer to the HIV Crisis," J. Hum. Lact. 15(4):345-346 (1999).
Virus Safety Services, Sanquin Research, Final Report FR4500, "Process Validation Breast Milk Step 1 for Inactivation of BVDV/HAV/HIV/PSR," May 27, 2002. pp. 1-33.
Voyer, M., et al. "Human Milk Lacto-Engineering," Acta Paediatr. Scand. 1984. vol. 73, pp. 302-306.
Williams et al., "Human Milk Banking," J. Trop. Pediatr. 31:185-190 (1985).
Young, "International Search Report," and "Written Opinion of the International Searching Authority," 11 pages, from International Patent Application No. PCT/US09/66430, United States Patent and Trademark Office, Alexandria, Virginia, USA (mailed Jan. 26, 2010).
Young, "International Search Report," and "Written Opinion of the International Searching Authority," 6 pages, from International Patent Application No. PCT/US07/19234, United States Patent and Trademark Office, Alexandria, Virginia, USA (mailed Jan. 18, 2008).
Young, "International Search Report," and "Written Opinion of the International Searching Authority," 8 pages, from International Patent Application No. PCT/US07/86973, United States Patent and Trademark Office, Alexandria, Virginia, USA (mailed May 5, 2008).
Young, "International Search Report," and "Written Opinion of the International Searching Authority," 8 pages, from International Patent Application No. PCT/US07/85969, United States Patent and Trademark Office, Alexandria, Virginia, USA (mailed May 8, 2008).
Young, "International Search Report," and "Written Opinion of the International Searching Authority," 8 pages, from International Patent Application No. PCT/US06/36827, United States Patent and Trademark Office, Alexandria, Virginia, USA (mailed Sep. 5, 2007).
Lapillione, et al., "Mineral balance and whole body bone mineral content in very low-birth-weight infants", (1994) Acta Pediatrica 84 (s405):117-122.
Melegh, et al., "Changes of Plasma Free Amino Acids and Renal Clearances of Carnitines in Premature Infants During L-Carnitine-Supplemented Human Milk Feeding", (1998) J. Pediatric Gastroenterol. Nutr. 7(3):424-429.
Salle, et al.,"Effects of Calcium and Phosphorus Supplementation on Calcium Retention and Fat Absorption in Preterm Infants Fed Pooled Human Milk", (1986) J. Pediatric Gastroenterol. Nutr. 5(4):638-642.

(56) References Cited

OTHER PUBLICATIONS

Martinez-Ferez, et al., "Goats' milk as a natural source of lactose-derived oligosaccharides: Isolation by membrane technology," International Dairy Journal, 16:173-181, 2006.

Morrow, et al., "Human-Milk Glycans Thant Inhibit Pathogen Binding Protect Breast-feeding Infants against Infectious Diarrhea," The Journal of Nutirition, 135:1304-1307 (2005).

Newburg, et al., "Fucosylated Oligosaccharides of Human Milk Protect Suckling Mice from Heat-Stabile Enterotoxin of *Escherichia coli*," The Journal of Infectious Diseases, 162:1075-1080, 1990.

Ninoneuvo, et al., "A Strategy for Annotating the Human Milk Glycome," Journal of Agricultural and Food Chemistry, 54:7471-7480, 2006.

Japanese Decision of Rejection, JP Application 2011-538734, mailing date Apr. 23, 2014, 3 pages.

* cited by examiner

HUMAN MILK PERMEATE COMPOSITIONS AND METHODS OF MAKING AND USING SAME

This application claims priority under 35 U.S.C. §371 to, and is a U.S. national phase application of, International Application No. PCT/US2009/066430, filed Dec. 2, 2009, which claims priority to U.S. Provisional Application No. 61/193,546, filed Dec. 5, 2008 and U.S. Provisional Application No. 61/119,176, filed Dec. 2, 2008, all of which are incorporated herein in their entireties.

TECHNICAL FIELD

This disclosure is related to human milk permeate compositions, e.g., compositions comprising human milk oligosaccharides, and methods of making and using such compositions.

BACKGROUND

Human milk is generally the food of choice for preterm and full term infants because of its nutritional composition and immunologic benefits. The source of human milk can be, e.g., a donor or the infant's mother. The nutritional value of raw or conventionally-processed donor milk, however, varies and, in most instances, is not sufficient to meet the needs of preterm infants. In addition, a possibility of bacterial, viral and other contamination of raw donor milk exists. Even the mother's own milk is often not nutritionally sufficient for the premature infant. It is often desirable to feed preterm infants milk that is fortified with various supplements, e.g., oligosaccharides. Compositions that contain human milk oligosaccharides can also be useful as supplements for infants, children, and adults who have or are at risk of developing various disorders and diseases, e.g., infections or immune deficiencies, and who need to develop and/or maintain proper gut flora.

SUMMARY

This disclosure features human milk permeate compositions, e.g., compositions that include human oligosaccharides, peptides, and other small molecules, and methods of making and using such compositions. The permeate compositions can contain various levels of nutritional components and can be used in feeding preterm and full term infants, as well as children and adults with various disorders and/or diseases. The compositions are generated from, inter alia, filtered portions of human milk. The present inventors have found that surprisingly, permeate (which had been thought to be a waste product lacking significant nutritional value) contains high biologically active content, including human oligosaccharides. It was found that the oligosaccharide content of the permeate and the human milk products described in application U.S. Ser. No. 11/947,580 (2008/0124430), both natural and concentrated, did not differ substantially with respect to size and composition as compared to mother's milk. Because the starting material, from which permeate is obtained, is pooled human milk, permeate and other processed human milk products (e.g., those described in application U.S. Ser. No. 11/947,580) can contain more varieties of oligosaccharides than individual mother's milk. Therefore, the permeate can be added to non-human (e.g. bovine) and/or human milk to increase its nutritional and/or immunologic value. The permeate can also be used to fight infections, treat inflammatory bowel disease and help develop and maintain proper gut flora. The permeate can also be diluted or concentrated and used in such forms as a nutritional supplement. Similar benefits can be obtained from permeate obtained by processing pooled human milk and administering it to infants, e.g., premature infants (e.g., pooled human milk described in application U.S. Ser. No. 11/947,580).

The methods featured herein are used to process large volumes of donor milk, e.g., about 75-2,000 liters/lot of starting material.

In a first aspect, the present invention provides a composition comprising milk and a human milk permeate. In one embodiment, the milk is human milk. In another embodiment, the milk is non-human milk. In some embodiments, the non-human milk is bovine milk. In some embodiments, the permeate of the composition is obtained by filtering liquid from human milk. In some embodiments, the composition is obtained by filtering liquid from human skim milk. In some embodiments, the composition further comprises vitamins and minerals.

In a second aspect, the present invention provides a nutritional composition comprising a concentrated or diluted human milk permeate. In one embodiment, the permeate is obtained by filtering liquid from human milk. In other embodiments, the permeate is obtained by filtering liquid from human skim milk. In some embodiments, the composition further comprises vitamins and minerals.

In a third aspect, the present invention provides a method of making a concentrated or a diluted human milk permeate, comprising (a) obtaining human milk, (b) separating the milk into cream and skim; (c) filtering the skim to obtain a permeate; (d) retaining the permeate; and (e) diluting, concentrating or drying the permeate. In some embodiments the diluting step in (e) comprises adding a non-human milk to the permeate. In some embodiments, the non-human milk is bovine milk. In other aspects of the invention, the diluting step in (e) comprises adding water or a buffer to the permeate. In some embodiments, the concentrating step in (e) comprises reverse osmosis. In some embodiments, the method of making a concentrated or diluted human milk permeate further comprises adding vitamins and minerals to the permeate after step (d). In some embodiments, the filtering in step (c) comprises ultrafiltration. In some embodiments, the method of making a concentrated or diluted human milk permeate further includes (f) reducing the bioburden. In some embodiments, reducing the bioburden comprises pasteurization or sterile filtration.

In a fourth aspect, the present invention provides a method of administering a permeate composition to a subject comprising human milk oligosaccharides to a subject comprising (a) obtaining human milk; (b) separating the milk into cream and skim; (c) filtering the skim to obtain a permeate; (d) retaining the permeate; and (e) administering the permeate to the subject. In some embodiments, the subject is a human preterm or full term infant. In some embodiments, the composition is administered topically or orally. In some embodiments, the composition is administered orally via a feeding tube.

In a fifth aspect, the present invention provides a method of establishing beneficial gut flora in a subject comprising administering a permeate composition comprising oligosaccharides from human milk to a subject. In some embodiments, the subject is a human. In some embodiments, the subject is a human preterm or full term infant. In some embodiments, the human preterm or full term infant is fed formula after birth. In some embodiments, the composition is administered prior to, concurrently with, or following other compositions useful for establishing beneficial gut flora. In some embodiments, the other compositions useful for establishing beneficial gut flora are probiotic bacteria or plant polysaccharides. In some embodiments, the composition is administered in conjunction with a non-human milk formulation. In some embodiments, the composition is in a mixture with a non-human milk formulation. In some embodiments, the composition is a human milk ultrafiltration permeate. In some embodiments, the permeate is obtained by filtering human milk. In some embodiments, the permeate is obtained by filtering human skim milk. In some embodiments, establishing beneficial gut flora comprises populating the gut with bifidobacteria or lactobacilli or both.

In a sixth aspect, the present invention provides a method of treating a subject who has an infection or is at risk of developing an infection comprising administering a permeate composition comprising oligosaccharides from human milk to the subject. In some embodiments, the symptoms of the infection are caused by bacteria, bacterial toxins or viruses. In some embodiments, the subject is a human. In some embodiments, the subject is a human neonate, infant, child or an adult. In some embodiments, treating comprises ameliorating at least one symptom of the infection. In some embodiments, treating comprises promoting the development of beneficial gut bacteria. In some embodiments, the beneficial gut bacteria are bifidobacteria or lactobacilli or both.

In a seven aspect, the invention provides a method of treating a subject suffering from an inflammatory bowel disease, the method comprising administering a permeate composition comprising oligosaccharides from human milk to a subject. In some embodiments, the inflammatory bowel disease is one or more of Crohn's disease, irritable bowel disease, ulcerative colitis (UC), indeterminate colitis, microscopic colitis, collagenous colitis and pseudomembrenous colitis. In some embodiments, the subject is a human. In some embodiments, the subject is a human neonate, infant, child or an adult. In some embodiments, treating comprises ameliorating at least one symptom of the inflammatory bowel disease. In some embodiments, treating comprises promoting development of beneficial gut bacteria. In some embodiments, the beneficial gut bacteria are bifidobacteria or lactobacilli or both.

In an eighth aspect, the invention provides a method of making a nutritional supplement comprising obtaining a permeate composition comprising oligosaccharides from human milk and supplementing a non-human milk formulation with the composition. In some embodiments, the composition is a concentrated or diluted human milk permeate composition. In some embodiments, the permeate composition is obtained by filtering liquid from human milk. In some embodiments, the permeate composition is obtained from filtering liquid from the skim portion of human milk.

In a ninth aspect, the invention provides a method of making a concentrated or diluted human milk permeate comprising (a) obtaining human milk; (b) separating the milk into cream and skim; (c) filtering the skim to obtain a permeate; (d) retaining the permeate; and (e) diluting, concentrating, or drying the permeate. In some embodiments, the diluting step (e) comprises adding a non-human milk composition to the permeate. In some embodiments, the non-human milk is bovine milk. In some embodiments, the diluting step in (e) comprises adding deionized water or a buffer. In some embodiments the concentrating step in (e) comprises reverse osmosis. In some embodiments, the method further comprises adding vitamins and minerals to the permeate after step (d). In some embodiments, the filtering in step (c) comprises ultrafiltering. In some embodiments, the method further comprises (f) reducing the bioburden. In some embodiments, reducing the bioburden comprises pasteurization or sterile filtration.

All patents, patent applications, and references cited herein are incorporated in their entireties by reference.

DETAILED DESCRIPTION

This disclosure features human milk permeate compositions, e.g., compositions that include human oligosaccharides, peptides, and other small molecules and methods of making and using such compositions. The compositions contain various levels of nutritional components and can be used in feeding of or administration to preterm and full term infants, as well as children and adults with various disorders and/or diseases. The compositions are generated from, inter alia, filtered portions of human skim milk. The present inventors have found that, surprisingly, permeate (which had been thought to be a waste product lacking significant nutritional value) contains high biologically active content, including human oligosaccharides. Because the starting material, from which permeate is obtained, is pooled human milk, permeate can contain more discrete molecular forms or types of oligosaccharides than individual mother's milk.

The permeate can be added to non-human or human milk to increase its nutritional value. For example, the permeate can be added to human milk fortifiers and standardized milk compositions described in application U.S. Ser. No. 11/947,580, filed on Nov. 29, 2007, the contents of which are incorporated herein by reference in their entirety. The permeate can also be added to non-human milk formula, e.g., bovine milk formulations or mixtures of human and non-human milk formulations. Without being bound by theory, it is believed by the inventors that permeate compositions comprising human milk oligosaccharides, peptides, and other small molecules can be used to promote development of beneficial gut flora in preterm infants or neonates and to maintain proper gut flora in children and adults. Permeate can also be useful as a supplement for infants, children, and adults who have or are at risk of developing various disorders and diseases, e.g., infections or immune deficiencies. The permeate can be diluted or concentrated and/or fortified with vitamins and minerals and used in such forms as a nutritional supplement.

The methods featured herein are used to process large volumes of donor milk, e.g., about 75-2,000 liters/lot of starting material. The compositions of the present disclosure are generated from human donor milk, e.g., pooled milk, which undergoes rigorous genetic screening and processing (e.g., to reduce the bioburden).

By "permeate" (also referred to herein as "permeate composition" or a "milk processing byproduct" or "milk byproducts") is meant a portion of milk that has been processed by filtration, e.g., ultrafiltration, of human milk, e.g. skim milk. Typically, the screen size used in ultrafiltration is 1 Kda-1,000 Kda in size. The liquid passing through the filtration contains a significant amount of oligosaccharides and is referred to as permeate.

By "whole milk" is meant milk from which no fat has been removed.

By "skim milk" is meant milk from which at least 75% of fat has been removed.

The terms "premature", "preterm" and "low-birth-weight (LBW)" infants are used interchangeably and refer to infants born less than 37 weeks gestational age and/or with birth weights less than 2500 gm.

The term "full term" infant is used to refer to infants born after 37 weeks gestational age and/or with birth weights greater than 2500 gm. By "bioburden" is meant microbiological contaminants and pathogens (generally living) that can be present in milk, e.g., viruses, bacteria, mold, fungus and the like.

Permeate Compositions and Methods of Obtaining Said Compositions

Permeate compositions featured herein are obtained from human milk, e.g., pooled donor milk. Methods of obtaining and screening human donor milk (including qualifying donors) are described in applications U.S. Ser. No. 11/947,580, and U.S. Ser. No. 11/526,127 (2007/0098863), the contents of which are incorporated herein by reference in their entirety.

Figure 1:
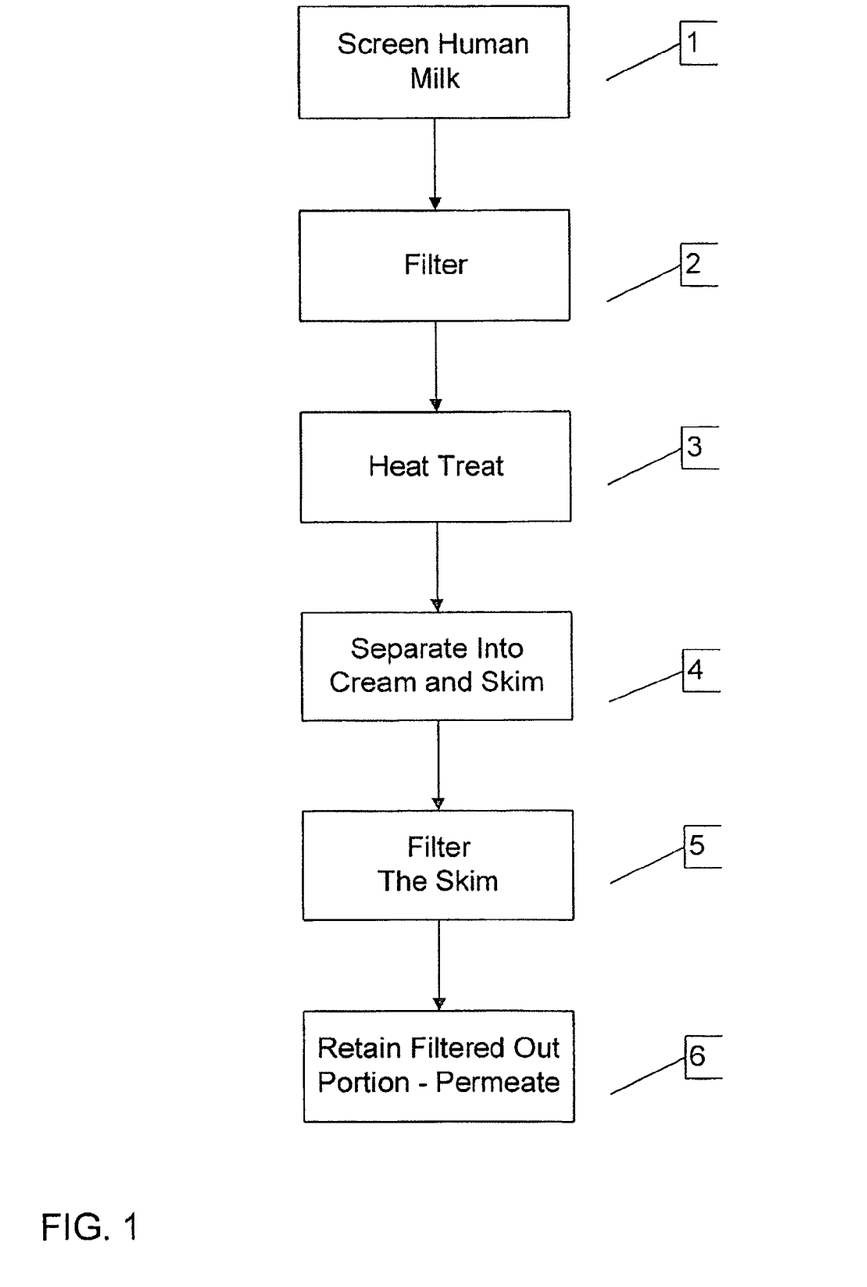
FIG. 1 is a chart of an embodiment of a method of making human milk permeate.

FIG. 1 shows one embodiment of a method of obtaining human milk permeate. As discussed above, donor milk is carefully analyzed for both identification purposes and to avoid contamination. The donor milk is frozen and, when desired, thawed and pooled. It is then screened (step 1 of FIG. 1), e.g., genetically screened, e.g., by polymerase chain reaction (PCR). Genetic screening is done to identify any contaminants, e.g., viral, e.g., HIV-1, HBV, and/or HCV. The milk then undergoes filtering, e.g., through about a 200 micron filter (step 2), and heat treatment (step 3). For example, the composition can be treated at about 63° C. or greater for about 30 minutes or more. In step 4, the milk is transferred to a separator, e.g., a centrifuge, to separate the cream from the skim. The skim can be transferred into a second processing tank where it remains at about 2 to 8° C. until a filtration step (step 5). Optionally, the cream separated from the skim in step 4, can undergo separation again to yield more skim.

Following separation of cream and skim (step 4), a desired amount of cream can be added to the skim, and the composition undergoes further filtration (step 5), e.g., ultrafiltration, e.g., with a pore size between 1-1000 Kda. This process concentrates the nutrients in the skim milk by filtering out the what was previously thought to be generally water or referred to as permeate. The present inventors have discovered, however, that the permeate retains a significant amount of oligosaccharides and can itself be used, e.g., as a nutritional supplement or in other ways described herein.

Figure 7:
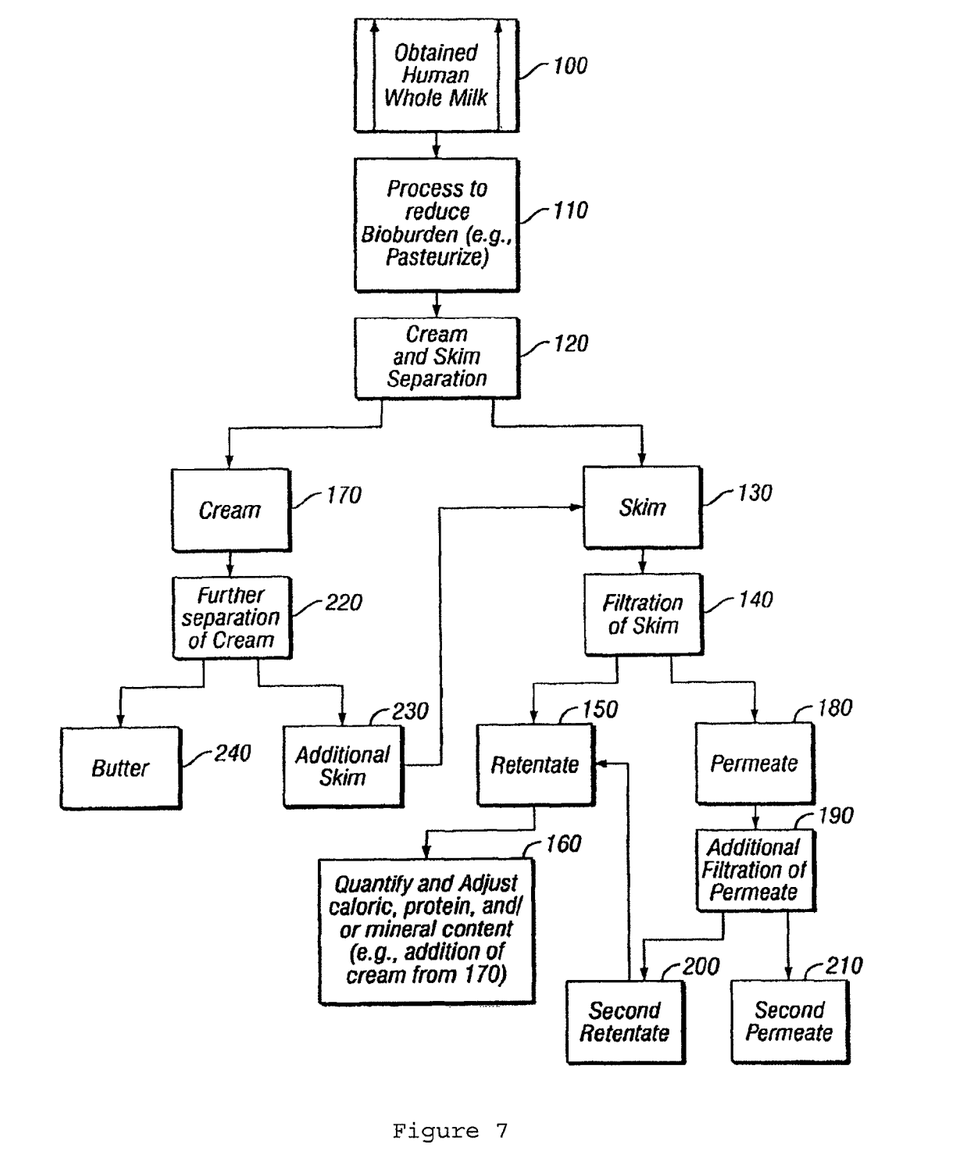
FIG. 7 is a graphical representation of the process of separating permeate from collected whole human milk.

Skim milk can undergo further processing for a human milk fortifier or standardized human milk composition, as described, e.g., in U.S. Ser. No. 11/947,580. For example, the skim can be blended with cream to obtain bulk final product, pasteurized and processed for bioburden. The permeate is retained (step 6) and can be used as a nutritional supplement. FIG. 7 also depicts the production of a "permeate" and a "second permeate," the latter produced by additional filtration of the "permeate."

The permeate can be further processed, e.g., concentrated or diluted and/or pasteurized. The permeate can be frozen and stored for future use. The permeate can be concentrated by reverse osmosis or dried using techniques familiar to those versed in the art. The resulting liquid products could then be pasteurized, sterile filtered, or subjected to other bioburden reduction steps. The product would then be filled into the final product container.

The permeate can also be supplemented with vitamins and/or minerals, e.g., calcium, chloride, zinc, copper, iron, manganese, magnesium, phosphorus, potassium, sodium, selenium, chromium, molybdenum, iodine, taurine, carnitine, choline, vitamin A, vitamin B1, vitamin B2, vitamin B6, vitamin B12, vitamin C, vitamin D, vitamin E, vitamin K, biotin, folic acid, pantothenic acid, niacin, and m-inositol. Vitamins and minerals are important, e.g., for proper nutrition and development of an infant. Trace minerals are associated with cell division, immune function and growth. Some key trace minerals include copper, magnesium, and iron (which is important, e.g., for the synthesis of hemoglobin, myoglobin and iron-containing enzymes). Zinc is needed, e.g., for growth, for the activity of numerous enzymes, and for DNA, RNA and protein synthesis. Copper is necessary for, e.g., the activity of several enzymes. Manganese is needed, e.g., for the development of bone and cartilage and is important in the synthesis of polysaccharides and glycoproteins. Vitamin A is a fat-soluble vitamin essential for, e.g., growth, cell differentiation, vision and proper functioning of the immune system. Vitamin D is important, e.g., for absorption of calcium and to a lesser extent, phosphorus, and for the development of bone. Vitamin E (tocopherol) prevents peroxidation of polyunsaturated fatty acids in the cell, thus preventing tissue damage. Folic acid plays a role in, e.g., amino acid and nucleotide metabolism. Thus, the permeate compositions can be supplemented with various minerals and/or vitamins, as desired.

Applications

The present disclosure features compositions that include human milk permeate and methods of using such compositions. The permeate compositions can be obtained, e.g., as described above by filtering liquid from skim milk. The compositions contain a significant number of human oligosaccharides, fucosilated and/or sialilated as described in Example 1 below. Human milk also contains peptides and other small molecules that can also be present in the permeate, e.g., can be obtained by varying the pore size during ultrafiltration. Because permeate is derived from pooled human milk, it can contain more forms of oligosaccharides than found in individual mother's milk. The permeate compositions can be used alone or in conjunction with other milk compositions, e.g., human milk compositions described in U.S. Ser. No. 11/947,580 and non-human milk formulas. Permeate or human and non-human milk formulas supplemented with permeate can be administered to pre-term or full tem infants to, e.g., promote development of proper gut flora, treat conditions characterized by immunodeficiency, and treat or prevent infections. Permeate can also be administered to children and adults alone or in conjunction with probiotics to promote beneficial gut flora, treat conditions characterized by immunodeficiency, and treat or prevent infections. Permeate compositions can be administered, e.g., orally or topically to treat skin conditions.

Human Milk Oligosaccharides

Many factors can affect the clinical outcome of a newborn, e.g., prematurely born, infant. Preterm infants have vulnerable immune systems, immature digestive systems, and increased total caloric and specific nutrient needs (when generally compared with full term infants). Thus, nutrition provided to such infants is an important factor in their growth and development. Human milk has long been recognized as the ideal food for preterm and full term infants because of its nutritional composition and immunologic benefits. Not every mother, however, can or will breastfeed her baby (or use a breast pump and store her milk). For example, mothers who have certain diseases, e.g., active tuberculosis, or are being administered radioisotopes, antimetabolites, or chemotherapy may not breast feed their infants. In addition, mother's own milk may not contain sufficient nutritional content to sustain a preterm infant. Use of donor milk can also be problematic, as such milk may not contain adequate nutrition for a preterm infant.

The present disclosure features permeate compositions that include oligosaccharides from pooled human milk, and methods of using such compositions to benefit, e.g., of premature human infants, full term infants, children, and adults.

Human milk oligosaccharides are carbohydrates that contain lactose at the reducing end and, typically, a fucose or a sialic acid at the nonreducing end. (Morrow et al., J. Nutrit. 135:1304-07, 2005). These terminal sugars are the residues that most strongly influence the selective growth of bacteria and the interaction of oligosaccharides with other molecules or cells, including bacterial pathogens in the gut lumen. For example, sialic acids are structural and functional components of brain gangliosides and have been implicated in neurological development of infants. Oligosaccharides can be free or conjugated as glycoproteins, glycolipids etc. and are classified as glycans. They constitute the third most numerous solid component of human milk, after lactose and lipid (Morrow et al.). The majority of these milk oligosaccharides, however, are not digestable by infants and can be found in infant feces largely intact. The present disclosure describes various uses of these oligosaccharides present in human milk permeate (which, in fact, contains a wide variety of oligosaccharides as it is derived from a pool of donated milk), which was previously thought to be a waste product of processing human milk. The permeate or compositions obtained from the permeate can be used (alone or in combination with human and non-human milk formulations or in combination with drugs or prebiotics), e.g., to promote beneficial gut flora, fight infections, ameliorate symptoms of conditions characterized by immunodeficiency, and provide additional nutrition. These compositions can be beneficial to recipients of various ages: from preterm infants through children to adults.

Gut Flora

Human gut flora, i.e., bacteria found in the gut, serves various functions, including digestion of certain polysaccharides and development of the gut's mucosal immune system. Gut bacteria can stimulate the lymphoid tissue associated with the gut mucosa to produce antibodies to pathogens, leaving the helpful species alone, a tolerance developed in infancy.

The gastrointestinal tract of a normal fetus is sterile. During birth and soon thereafter, the infant's gut is colonized by various bacteria. The sources of the bacteria can be the mother's body and/or the environment. After birth, various bacteria can be transferred from the mother to the infant through suckling and touching. Most infant GI tracts are initially colonized by large numbers of *E. coli* and *Streptococci*. Eventually, breast-fed babies become dominated by bifidobacteria, while formula-fed infants have a variety of bacteria, including Enterobacteriaceae, Enterococci, bifidobacteria, Bacteroides, and Clostridia in the gut. After the introduction of solid food and weaning, the microflora of breast-fed infants becomes similar to that of formula-fed infants. By about two years, the fecal microflora of children is similar to that of adults.

Given the importance of gut flora, it is crucial to develop a beneficial bacterial population at birth and maintain it throughout childhood and adult life. The compositions and methods featured herein can help in the establishment and maintenance of such beneficial gut flora.

The compositions that include human milk oligosaccharides, e.g., human milk permeate or compositions derived from human milk permeate, can be administered to preterm infants, full term infants, children, and adults. They can be administered alone or in combination with other compositions that aid in establishing beneficial gut flora, e.g., probiotic bacteria or prebiotic plant polysaccharides, to form a symbiotic composition. They can be administered as part of human milk formulations (e.g., compositions described in application U.S. Ser. No. 11/947,580) or non-human milk baby formulas. Without being bound by theory, it is believed that the present permeate compositions can promote colonization of the gut by lactobacilli and/or bifidobacteria. Both lactobacilli and bifidobacteria are known as probiotics—bacteria that protect their host and prevent disease. Bifidobacteria are anaerobic bacteria that aid in digestion and have been associated with reduced incidence of allergies and cancer prevention. Lactobacilli are bacteria that convert lactose and other sugars to lactic acid and may possess anti-inflammatory and anti-cancer properties.

Additionally, the human milk permeate or compositions derived from human milk permeate of the current invention containing human milk oligosaccharides can be administered to children or adults for the treatment of inflammatory bowel disease. Inflammatory bowel disease is a collective term encompassing related, but distinct, chronic inflammatory disorders of the gastrointestinal tract, such as Crohn's disease, irritable bowel disease, ulcerative colitis, indeterminate colitis, microscopic colitis, and collagenous colitis. It has been found that patients suffering from active Crohn's disease have significantly less recoverable bifidobacteria in their feces compared with healthy individuals. This reduction in bifidobacteria numbers was observed to be directly correlated with decreased levels of $\beta$-D galactosidase production and activity (Favier, C. et at, Dig. Dis. Sci. 1997; 42:817-822). $\beta$-D galactosidase is an enzyme produced by bifidobacteria. These results support suggestions proposed in other studies that strains of bifidobacteria may play important roles in maintaining a balanced healthy intestinal microflora. Therefore, according to the present invention, the colony promotion of colonization of bifidobacteria in the gut by the oligosaccharide rich permeate of the current invention can be useful in ameliorating the symptoms of inflammatory bowel disease. Similarly, the compositions of the current invention can be useful in treating pseudomembrenous colitis (also known as *C. difficile*-related colits), a common complication of prolonged broad-spectrum antibiotic treatment that is due to overgrowth of normal flora by a toxin-producing strain of *C. difficile*. The permeate compositions of the current invention can be administered before during or after any other treatment for inflammatory bowel disease including probiotic formulations, anti-inflammatory medications or immunomodulators.

Infections

Human milk oligosaccharides are thought to serve various anti-infective functions, e.g., inhibit pathogen binding. Thus, the permeate compositions featured herein and containing a wide variety of human milk oligosaccharides (as they are derived from pooled human milk) can be used to protect infants, children, and adults from various types of infection. For example, preterm and full term infants administered the present compositions can be protected from infectious diarrhea, necrotizing enterocolitis (NEC), respiratory tract infections, bacteremia, meningitis and others. Children and adults can likewise benefit from administration of the compositions. The compositions can be administered after an onset of an infection, to ameliorate and/or eliminate its symptoms or prior to infection (for individuals thought to be at risk). The compositions can be administered via various means, including orally or topically (e.g., to treat skin infections and other skin conditions).

In general, the permeate compositions featured herein can be administered to subjects, e.g., human subjects of various ages, for any condition or disorder that would be ameliorated or eliminated by application of oligosaccharides, peptides, or other small molecules derived from human milk.

Kits

The present disclosure also features kits that include the human milk permeate compositions described herein and containers for mixing the compositions with raw human milk or non-human milk. The containers can include bottles, e.g., graduated bottles to assist in proper dilution, syringes, cans, and other containers known in the art.

The embodiments of the disclosure may be carried out in other ways than those set forth herein without departing from the spirit and scope of the disclosure. The embodiments are, therefore, to be considered in all respects as illustrative and not restrictive.

EXAMPLE 1

Collection and Analysis of Human Milk Permeate

Breast milk was collected from screened donors throughout the U.S. and stored at −20° C. for up to 12 months. Pooled donor human milk was processed and various samples analyzed for their oligosaccharide composition. Pools from 20-50 donors were used to produce human milk fortifier compositions described in application U.S. Ser. No. 11/947,580.

Before processing, a sample of initial pooled donor milk was set aside for analysis (sample 49 in Table III). The pooled milk was screened, filtered, heat-treated, separated into skim and cream, and the skim was ultrafiltered. A portion of the filtered-out composition, the permeate, was set aside for analysis (sample 53 in Table IV). The skim was blended with cream and pasteurized. A portion of the bulk final product was set aside for analysis (samples 42, 48, and 54 in Tables I, II, and V, respectively).

Each milk sample that was set aside for analysis (0.5 mL) was diluted with 0.5 mL of pure water and centrifuged at 4000 rpm at 4° C. for 30 minutes to separate fat. The permeate was analyzed undiluted. The fat-free fraction was treated with 4 volumes (2:1) of a chloroform-methanol solution (v/v). The emulsion was centrifuged at 3500 rpm for 30 min at 4° C., and the lower chloroform layer and denatured protein were discarded. The upper layer was collected, two volumes of pure ethanol were added and protein fraction was left to precipitate at 4° C. overnight.

After protein separation by centrifugation at 3500 rpm for 30 min at 4° C., the limpid upper solution was collected and freeze-dried. The resulting powder (freeze-dried oligosaccharide rich fraction) was used for oligosaccharide analysis. Oligosaccharides were reduced to alditol form using 1.0 M sodium borohydride in deionized water and incubated at 42° C. overnight. After the reaction, oligosaccharides were purified from contaminants by solid-phase extraction using a nonporous graphitized carbon cartridge (GCC-SPE). Nonporous graphitized carbon cartridges (150 mg of bed weight, 4 mL tube size) for desalting were purchased from Alltech (Deerfield, Ill., USA). Evaporation of solvents was performed using a speedvac centrifuge.

Solid Phase Extraction.

Prior to use, each GCC-SPE cartridge was washed with 3 column volumes of 80% acetonitrile in 0.05% trifluoroacetic acid (TFA) (v/v) followed by 3 column volumes of deionized water. After loading of the oligosaccharide mixture onto a cartridge, salts and residual peptides were removed by washing with 8 cartridge volumes of deionized water. The oligosaccharides were then eluted from the column using 10% acetonitrile in water (v/v) and 20% acetonitrile in water (v/v). Each fraction (6 mL) was collected and evaporated in vacuo prior to MS analysis.

Mass Spectrometric Analysis.

Matrix-assisted laser desorption/ionization (MALDI) Fourier transform-ion cyclotron resonance mass spectrometry (FT ICR MS) was performed on an HiResMALDI (IonSpec Corp., Irvine, Calif.) equipped with an external MALDI source, a 7.0 Tesla superconducting magnet and a pulsed Nd:YAG laser (355 nm). 2,5-Dihydroxybenzoic acid (DHB) was used as a matrix (5 mg/100 µL in a solution of 50% acetonitrile/50% water (v/v)). The solution of oligosaccharide (1 µL) was applied to the MALDI probe followed by addition of 0.01 M NaCl (0.5 µL) and the matrix solution (1 µL). The sample was dried under a stream of air and subjected to mass spectrometry.

Figure 2:
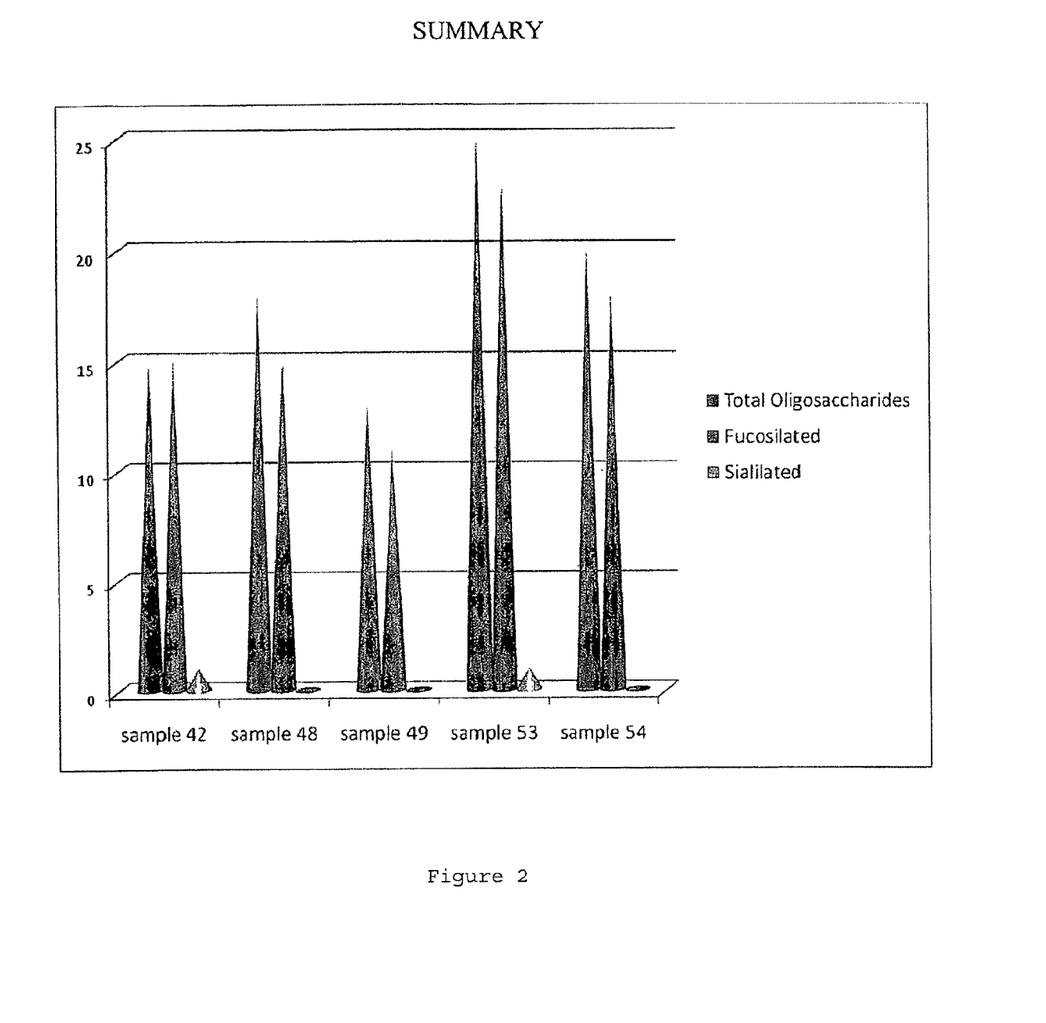
FIG. 2 is a chart showing a summary of oligosaccharide composition of samples 42, 48, 49, 53, and 54.
Figure 3:
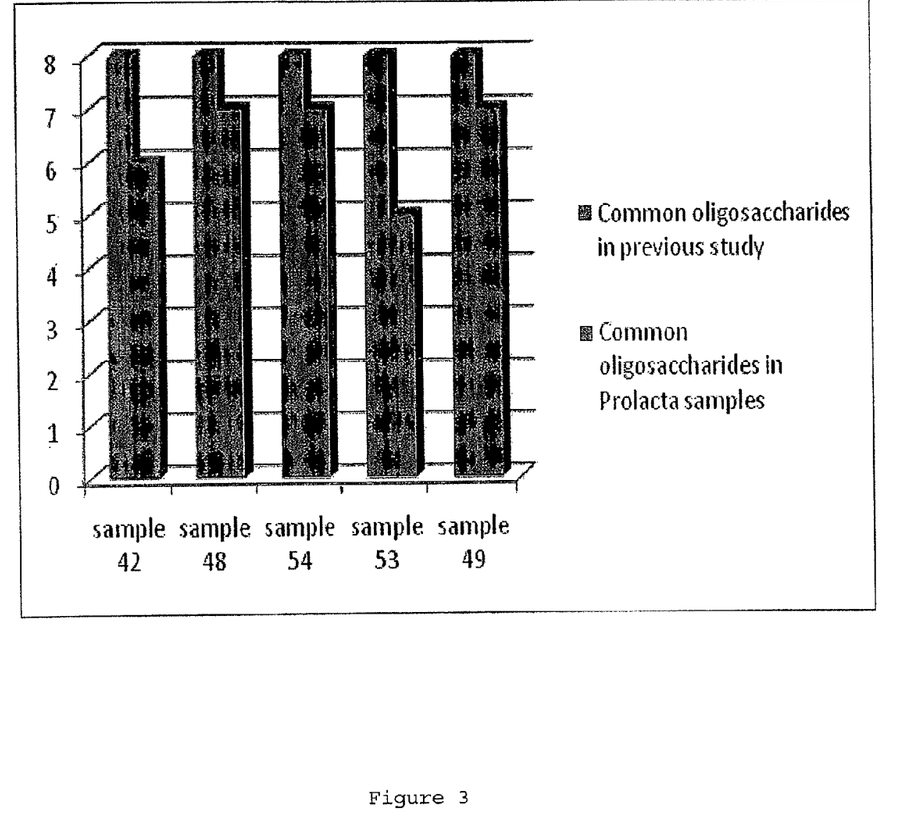
FIG. 3 is a histogram of common human milk oligosaccharides found in human milk and in samples 42, 48, 54 (all bulk final product), 53 (ultrafiltration permeate), and 49 (initial pool of donor milk).
Figure 4:
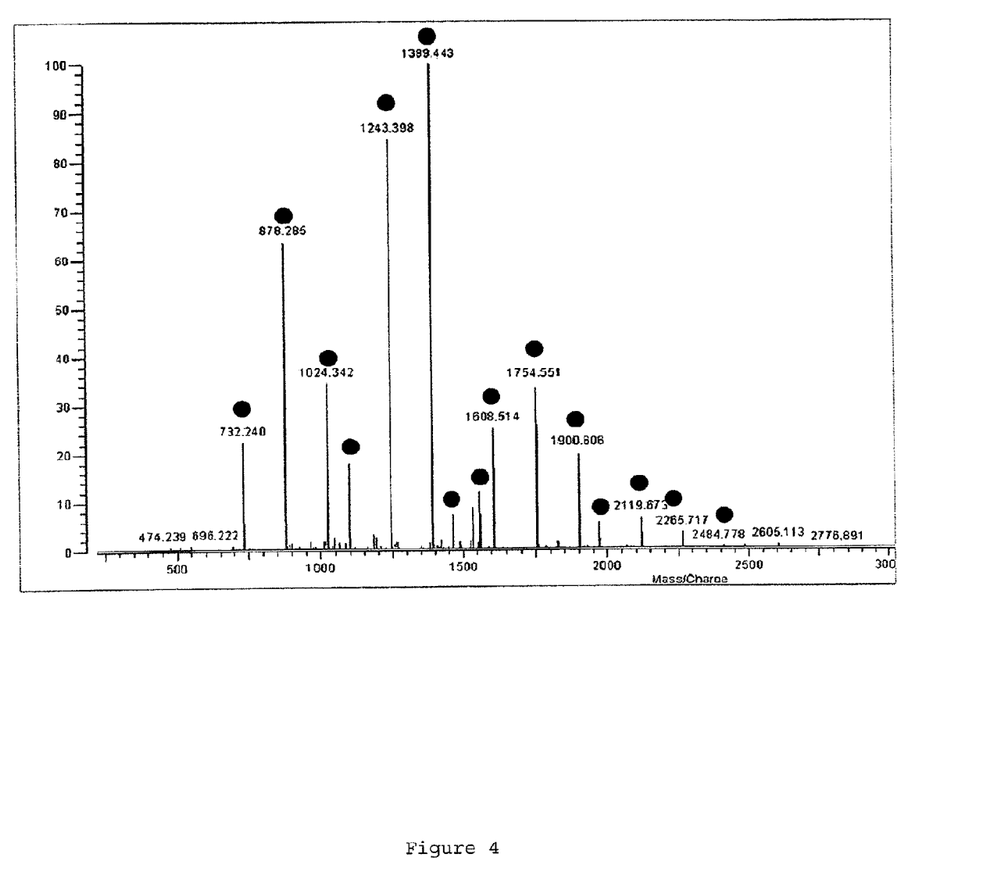
FIG. 4 is a graph showing a typical mass spectrometric profile of free oligosaccharides in human milk. Round dots represent human milk oligosaccharides.
Figure 5:
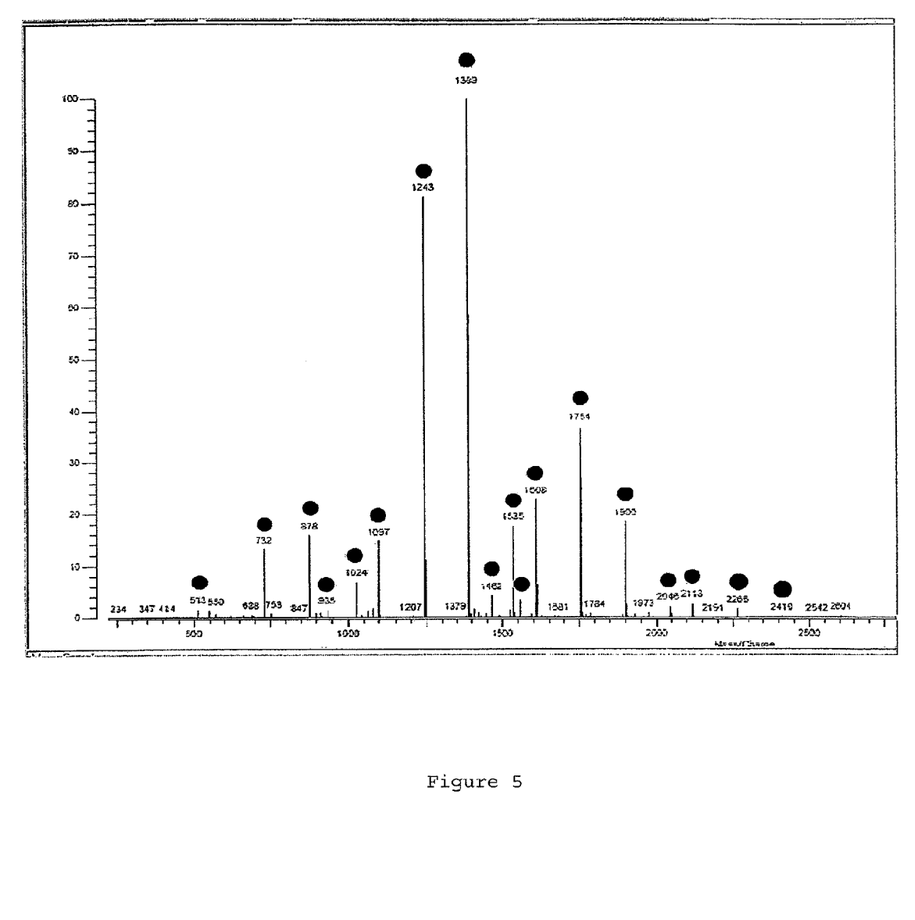
FIG. 5 is a graph showing mass spectrum profile obtained for sample 42 (PROLACT+™H2MF™) (See U.S. Ser. No. 11/947,580) Round dots represent human milk oligosaccharides.
Figure 6:
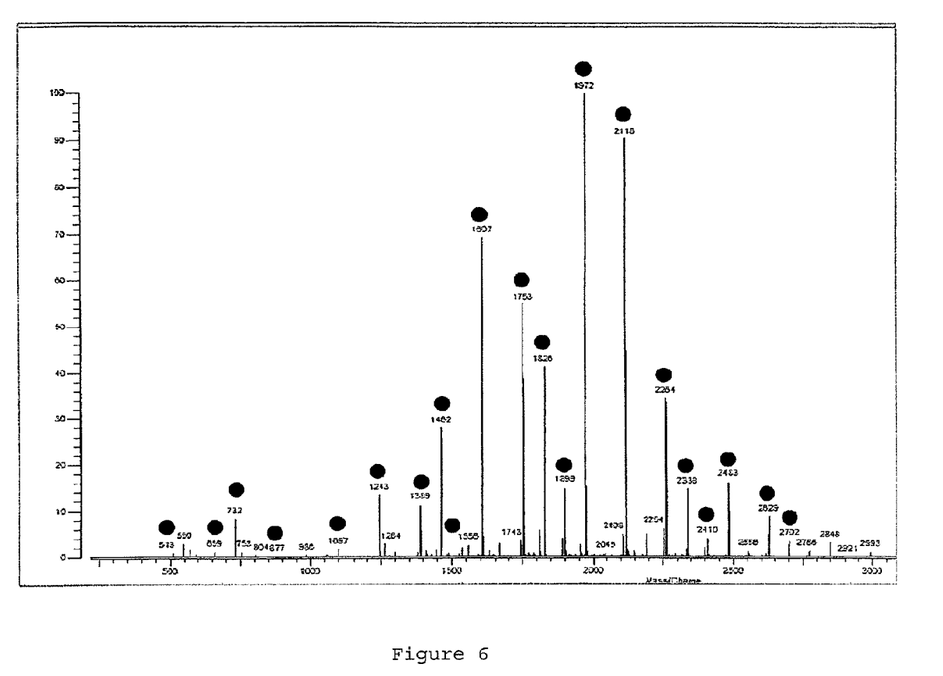
FIG. 6 is a graph showing mass spectrum profile obtained for sample 53 (PROLACT+™H2MF™ process byproduct or permeate) (See U.S. Ser. No. 11/947,580). Round dots represent human milk oligosaccharides.

The compositions of the various samples discussed above are presented in Tables I-IV, and a summary is shown in FIG. 2. The experimental mass:charge ratios (m/z expe) were matched to calculated mass:charge ratios (m/z cal) for known oligosaccharides in human milk. Mass spectrometric profiles of specific samples are shown in Tables III-V (human milk sample in Table III, bulk product in Table IV, and permeate in Table V). Mass spectrometric analyses of the five samples revealed a highly complex mixture of oligosaccharides, typical of human milk, and varying in size, composition, and abundance.

The oligosaccharides identified were from two main classes: (1) neutral oligosaccharides containing galactose, N-acetylglucosamine, lactose, and fuctose (Hex, HexNAc and Fuc); and (2) anionic oligosaccharides containing the same oligosaccharide compositions with the addition of N-acetylneuraminic acid (NeuAC). A previous investigation (Ninonuevo et al., J. Agric. Food Chem. 2008, 54: 7471-7480) identified diversity between individuals in the total numbers and relative abundances of specific oligosaccharides in unfiltered milk. Thus, the milk samples analyzed (natural or concentrated) confirmed that all samples show ostensibly most of the oligosaccharides previously found to be common in human milk from different donors.

TABLE I

SAMPLE 42 (BULK FINAL PRODUCT) OLIGOSACCHARIDES

| m/z expe | Hex | HexNAc | Fuc | NeuAC | m/z cal | Error | Mode | Form | abund. |
|---|---|---|---|---|---|---|---|---|---|
| 1389.477 | 4 | 2 | 2 | 0 | 1389.501 | −0.0246 | Na | Alditol | 100 |
| 1243.419 | 4 | 1 | 2 | 0 | 1243.443 | −0.0239 | Na | Alditol | 79.32 |
| 1754.611 | 5 | 2 | 3 | 0 | 1754.633 | −0.0228 | Na | Alditol | 36.36 |
| 1608.563 | 5 | 1 | 3 | 0 | 1608.576 | −0.013 | Na | Alditol | 22.4 |
| 1900.682 | 5 | 3 | 3 | 0 | 1900.691 | −0.0095 | Na | Alditol | 18.22 |
| 1535.545 | 4 | 3 | 2 | 0 | 1535.559 | −0.0144 | Na | Alditol | 17.4 |
| 878.3013 | 3 | 1 | 1 | 0 | 878.3111 | −0.0098 | Na | Alditol | 15.74 |
| 1097.368 | 4 | 0 | 2 | 0 | 1097.385 | −0.0176 | Na | Alditol | 14.48 |
| 732.245 | 3 | 0 | 1 | 0 | 732.2532 | −0.0082 | Na | Alditol | 13.02 |
| 1024.361 | 3 | 2 | 1 | 0 | 1024.369 | −0.0083 | Na | Alditol | 6.88 |
| 1462.514 | 5 | 0 | 3 | 0 | 1462.518 | −0.0041 | Na | Alditol | 4.29 |
| 1556.519 | 4 | 1 | 2 | 1 | 1556.521 | −0.0021 | 1 Na | Alditol | 3.48 |
| 2119.781 | 6 | 2 | 4 | 0 | 2119.766 | 0.0156 | Na | Alditol | 2.72 |
| 2046.765 | 5 | 4 | 3 | 0 | 2046.749 | 0.0154 | Na | Alditol | 2.24 |
| 1557.524 | 4 | 3 | 2 | 0 | 1557.541 | −0.0168 | 1 Na | Alditol | 2.21 |

TABLE II

SAMPLE 48 (BULK FINAL PRODUCT) OLIGOSACCHARIDES

| m/z expe | Hex | HexNAc | Fuc | NeuAC | m/z cal | Error | Mode | Form | abund. |
|---|---|---|---|---|---|---|---|---|---|
| 1389.474 | 4 | 2 | 2 | 0 | 1389.501 | −0.0274 | Na | Alditol | 100 |
| 1754.609 | 5 | 2 | 3 | 0 | 1754.633 | −0.0243 | Na | Alditol | 15.63 |
| 1462.519 | 3 | 5 | 1 | 0 | 1462.543 | −0.0239 | Na | Alditol | 1.27 |
| 1243.422 | 4 | 1 | 2 | 0 | 1243.443 | −0.0212 | Na | Alditol | 73.84 |
| 1405.476 | 5 | 1 | 2 | 0 | 1405.496 | −0.0202 | Na | Alditol | 1.45 |
| 1900.672 | 5 | 3 | 3 | 0 | 1900.691 | −0.0198 | Na | Alditol | 10.32 |
| 1535.54 | 4 | 3 | 2 | 0 | 1535.559 | −0.0196 | Na | Alditol | 23.25 |
| 1097.373 | 4 | 0 | 2 | 0 | 1097.385 | −0.0129 | Na | Alditol | 11.85 |
| 1608.567 | 5 | 1 | 3 | 0 | 1608.576 | −0.0089 | Na | Alditol | 6.79 |
| 1024.364 | 3 | 2 | 1 | 0 | 1024.369 | −0.0047 | Na | Alditol | 14.85 |
| 878.3075 | 3 | 1 | 1 | 0 | 878.3111 | −0.0036 | Na | Alditol | 24.05 |
| 2046.746 | 5 | 4 | 3 | 0 | 2046.749 | −0.0031 | Na | Alditol | 1.28 |
| 732.2536 | 3 | 0 | 1 | 0 | 732.2532 | 0.0004 | Na | Alditol | 14.72 |
| 1462.519 | 5 | 0 | 3 | 0 | 1462.518 | 0.0012 | Na | Alditol | 1.27 |
| 1081.392 | 3 | 1 | 2 | 0 | 1081.391 | 0.0015 | Na | Alditol | 1.99 |
| 513.1818 | 2 | 1 | 0 | 0 | 513.1789 | 0.0029 | Na | Alditol | 9.19 |
| 935.3364 | 3 | 0 | 2 | 0 | 935.3326 | 0.0038 | Na | Alditol | 1.26 |
| 659.2407 | 2 | 2 | 0 | 0 | 659.2368 | 0.0039 | Na | Alditol | 1.08 |

TABLE III

SAMPLE 49 (INITIAL POOL OF DONOR MILK) OLIGOSACCHARIDES

| m/z expe | Hex | HexNAc | Fuc | NeuAC | m/z cal | Error | Mode | Form | abund. |
|---|---|---|---|---|---|---|---|---|---|
| 1388.972 | 4 | 3 | 3 | 0 | 1388.99 | −0.0202 | Na | Alditol | 100 |
| 1754.608 | 5 | 2 | 3 | 0 | 1754.633 | −0.0258 | Na | Alditol | 5.1 |
| 1243.423 | 4 | 1 | 2 | 0 | 1243.443 | −0.0207 | Na | Alditol | 4.1 |
| 1900.671 | 5 | 3 | 3 | 0 | 1900.691 | −0.0202 | Na | Alditol | 1.48 |
| 1535.542 | 4 | 3 | 2 | 0 | 1535.559 | −0.0169 | Na | Alditol | 5.9 |
| 1608.562 | 5 | 1 | 3 | 0 | 1608.576 | −0.0139 | Na | Alditol | 3.6 |
| 1097.377 | 4 | 0 | 2 | 0 | 1097.385 | −0.0084 | Na | Alditol | 10.5 |
| 1024.364 | 3 | 2 | 1 | 0 | 1024.369 | −0.0054 | Na | Alditol | 14.7 |
| 1462.513 | 5 | 0 | 3 | 0 | 1462.518 | −0.0042 | Na | Alditol | 1.2 |
| 878.3073 | 3 | 1 | 1 | 0 | 878.3111 | −0.0038 | Na | Alditol | 26 |
| 732.2535 | 3 | 0 | 1 | 0 | 732.2532 | 0.0003 | Na | Alditol | 14.2 |
| 513.1826 | 2 | 1 | 0 | 0 | 513.1789 | 0.0037 | Na | Alditol | 8.9 |
| 659.241 | 2 | 2 | 0 | 0 | 659.2368 | 0.0042 | Na | Alditol | 1.66 |

TABLE IV

SAMPLE 53 (PERMEATE) OLIGOSACCHARIDES

| m/z expe | Hex | HexNAc | Fuc | NeuAC | m/z cal | Error | Mode | Form | abund. |
|---|---|---|---|---|---|---|---|---|---|
| 1973.685 | 6 | 1 | 4 | 0 | 1973.708 | −0.0229 | Na | Alditol | 100 |
| 2119.75 | 6 | 2 | 4 | 0 | 2119.766 | −0.0152 | Na | Alditol | 89.8 |
| 1608.564 | 5 | 1 | 3 | 0 | 1608.576 | −0.0116 | Na | Alditol | 69.33 |
| 1754.626 | 5 | 2 | 3 | 0 | 1754.633 | −0.0077 | Na | Alditol | 54.88 |
| 1827.651 | 6 | 0 | 4 | 0 | 1827.65 | 0.0009 | Na | Alditol | 41.26 |
| 2265.835 | 6 | 3 | 4 | 0 | 2265.824 | 0.0119 | Na | Alditol | 34.5 |
| 1462.52 | 5 | 0 | 3 | 0 | 1462.518 | 0.0022 | Na | Alditol | 28.01 |
| 1900.709 | 5 | 3 | 3 | 0 | 1900.691 | 0.0177 | Na | Alditol | 15.16 |
| 2484.931 | 7 | 2 | 5 | 0 | 2484.898 | 0.0334 | Na | Alditol | 15.12 |
| 2338.868 | 7 | 1 | 5 | 0 | 2338.84 | 0.028 | Na | Alditol | 14.2 |
| 1243.447 | 4 | 1 | 2 | 0 | 1243.443 | 0.0039 | Na | Alditol | 13.39 |
| 1389.508 | 4 | 2 | 2 | 0 | 1389.501 | 0.0069 | Na | Alditol | 11.41 |
| 732.2539 | 3 | 0 | 1 | 0 | 732.2532 | 0.0007 | Na | Alditol | 8.37 |
| 2631.035 | 7 | 3 | 5 | 0 | 2630.956 | 0.0792 | Na | Alditol | 4.85 |
| 2192.827 | 7 | 0 | 5 | 0 | 2192.782 | 0.0447 | Na | Alditol | 4.82 |
| 2411.932 | 6 | 4 | 4 | 0 | 2411.881 | 0.0504 | Na | Alditol | 3.39 |
| 2704.042 | 8 | 1 | 6 | 0 | 2703.972 | 0.0697 | Na | Alditol | 2.85 |
| 1556.543 | 4 | 1 | 2 | 1 | 1556.521 | 0.0227 | Na | Alditol | 2.67 |
| 2850.121 | 8 | 2 | 6 | 0 | 2850.03 | 0.0908 | Na | Alditol | 2.16 |
| 570.2012 | 2 | 0 | 1 | 0 | 570.2004 | 0.0008 | Na | Alditol | 1.94 |
| 1097.392 | 4 | 0 | 2 | 0 | 1097.385 | 0.0063 | Na | Alditol | 1.82 |
| 2557.988 | 8 | 0 | 6 | 0 | 2557.914 | 0.0739 | Na | Alditol | 1.28 |
| 1300.476 | 4 | 0 | 3 | 0 | 1300.465 | 0.011 | Na | Alditol | 1.19 |
| 659.2383 | 2 | 2 | 0 | 0 | 659.2368 | 0.0015 | Na | Alditol | 1.16 |
| 513.1802 | 2 | 1 | 0 | 0 | 513.1789 | 0.0013 | Na | Alditol | 1.01 |

TABLE V

SAMPLE 54 (BULK FINAL PRODUCT) OLIGOSACCHARIDES

| m/z expe | Hex | HexNAc | Fuc | NeuAC | m/z cal | Error | Mode | Form | abund. |
|---|---|---|---|---|---|---|---|---|---|
| 513.1576 | 2 | 1 | 0 | 0 | 513.1789 | −0.0213 | Na | Alditol | 12.82 |
| 659.2137 | 2 | 2 | 0 | 0 | 659.2368 | −0.0231 | Na | Alditol | 1.38 |
| 570.1783 | 2 | 0 | 1 | 0 | 570.2004 | −0.0221 | Na | Alditol | 4.24 |
| 878.2782 | 3 | 1 | 1 | 0 | 878.3111 | −0.0329 | Na | Alditol | 20.97 |
| 1024.338 | 3 | 2 | 1 | 0 | 1024.369 | −0.0309 | Na | Alditol | 8.82 |
| 732.2245 | 3 | 0 | 1 | 0 | 732.2532 | −0.0287 | Na | Alditol | 16 |
| 935.3093 | 3 | 0 | 2 | 0 | 935.3326 | −0.0233 | Na | Alditol | 1.16 |
| 1243.39 | 4 | 1 | 2 | 0 | 1243.443 | −0.0536 | Na | Alditol | 76.72 |
| 1389.445 | 4 | 2 | 2 | 0 | 1389.501 | −0.0567 | Na | Alditol | 100 |
| 1535.524 | 4 | 3 | 2 | 0 | 1535.559 | −0.0348 | Na | Alditol | 19.2 |
| 1097.334 | 4 | 0 | 2 | 0 | 1097.385 | −0.0511 | Na | Alditol | 14.86 |
| 1608.547 | 5 | 1 | 3 | 0 | 1608.576 | −0.029 | Na | Alditol | 19.86 |
| 1754.592 | 5 | 2 | 3 | 0 | 1754.633 | −0.0416 | Na | Alditol | 36.7 |
| 1900.669 | 5 | 3 | 3 | 0 | 1900.691 | −0.0225 | Na | Alditol | 24.32 |
| 2046.773 | 5 | 4 | 3 | 0 | 2046.749 | 0.0236 | Na | Alditol | 4.32 |
| 1462.497 | 5 | 0 | 3 | 0 | 1462.518 | −0.0204 | Na | Alditol | 3.8 |
| 1973.729 | 6 | 1 | 4 | 0 | 1973.708 | 0.0213 | Na | Alditol | 1.66 |
| 2119.792 | 6 | 2 | 4 | 0 | 2119.766 | 0.0261 | Na | Alditol | 4.15 |
| 2265.855 | 6 | 3 | 4 | 0 | 2265.824 | 0.0314 | Na | Alditol | 4.45 |
| 2411.941 | 6 | 4 | 4 | 0 | 2411.881 | 0.0596 | Na | Alditol | 1.3 | m/z expe: Mass/charge experimental,
m/z cal: mass/charge calculated,
Hex: hexose;
HexNAc: N-acetylhexosamine;
Fuc: fucose;
NeuAc: N-acetyl-neuraminic acid or sialic acid;

It appears that processed human milk product (fortifier or samples 42, 48, and 54) and permeate (sample 53) contain the full range of oligosaccharides commonly found in human milk. The selection and amounts of the individual oligosaccharides present in these samples reflect the relative amounts in the donor pool which average out the variation across individual donors.

Thus, according to the present invention, the permeate is a valuable source of human milk oligosaccharides that can be used as a nutritional or immunologic supplement for preterm infants, infants, children, and adults.

EXAMPLE 2

Oligosaccharide Profile of Pooled Permeate Samples

Six pooled permeate samples were analyzed for specific oligosaccharide content (Table VI). Each of the pooled permeate samples were derived from pooled milk received from multiple donors by the method discussed above in Example 1. The collected samples of permeate were analyzed by mass spectrometry by the method described above in Example 1, to detect the presence (1) or absence (0) of the specific oligosaccharides indicated. The oligosaccharides are represented in Table VI by their mass/charge ratios.

TABLE VI

| Olgios m/z expe | Permeate Sample #5 | Permeate Sample #11 | Permeate Sample #23 | Permeate Sample #28 | Permeate Sample #47 | Permeate Sample #53 |
|---|---|---|---|---|---|---|
| 513  | 0 | 0 | 1 | 0 | 1 | 0 |
| 732  | 1 | 1 | 1 | 1 | 1 | 1 |
| 878  | 1 | 1 | 1 | 1 | 1 | 1 |
| 935  | 0 | 0 | 1 | 0 | 0 | 1 |
| 1024 | 1 | 1 | 1 | 1 | 1 | 0 |
| 1097 | 1 | 1 | 1 | 1 | 1 | 1 |
| 1243 | 1 | 1 | 1 | 1 | 1 | 1 |
| 1389 | 1 | 1 | 1 | 1 | 1 | 1 |
| 1462 | 1 | 1 | 1 | 0 | 1 | 1 |
| 1535 | 0 | 0 | 1 | 0 | 1 | 0 |
| 1556 | 0 | 0 | 0 | 0 | 0 | 1 |
| 1608 | 1 | 0 | 1 | 1 | 1 | 1 |
| 1754 | 0 | 1 | 1 | 1 | 0 | 1 |
| 1827 | 1 | 0 | 0 | 0 | 0 | 1 |
| 1900 | 0 | 1 | 0 | 0 | 0 | 1 |
| 1973 | 1 | 0 | 0 | 1 | 0 | 1 |
| 2119 | 1 | 1 | 0 | 1 | 0 | 1 |
| 2192 | 0 | 0 | 0 | 0 | 0 | 1 |
| 2264 | 0 | 0 | 0 | 0 | 0 | 1 |
| 2338 | 0 | 0 | 0 | 0 | 0 | 1 |
| 2411 | 0 | 0 | 0 | 0 | 0 | 1 |
| 2485 | 0 | 0 | 0 | 0 | 0 | 1 |
| 2631 | 0 | 0 | 0 | 0 |   | 1 |

1 = oligosaccharide present in the sample
0 = oligosaccharide not detectable in the sample It appears as though, while there is overlap between the samples with respect to certain oligosaccharides (i.e. oligosaccharides 732, 878, 1097, 1243 and 1389 are present in all six samples), there are also many oligosaccharides present in certain samples while not present in other samples (i.e. oligosaccharide 935 is present in permeate numbers 23, and 53 but not permeate numbers 5, 11, 28 or 47). Therefore, additional pooling of the pooled permeate samples may be necessary in order to obtain a composition with substantially all or all oligosaccharide species represented.

EXAMPLE 3

Administration of Permeate Compositions

As discussed above, it is believed by the inventors that human milk permeate compositions from pooled milk can provide a wide variety of nutritional and immunologic benefits, as they are a source of a wider variety of oligosaccharides than those found in individual mother's milk. They can also contain various types of peptides and other beneficial small molecules.

The isolated human milk permeate compositions will be administered to infants, both preterm and full term infants, to promote their development of proper gut flora, ameliorate and/or eliminate infections. The study will investigate infants divided into 5 arms including infants receiving:

1. Mother's milk plus fortifier
2. Cow's milk plus permeate
3. Cow's milk plus strain 1 of bifidobacter
4. Cow's milk plus strain 2 of bifidobacter
5. Cow's milk plus non-milk derived fructose oligosaccharide Composition of infant feces will be monitored to determine the content of their gut flora. Infants suffering from infections caused by pathogens, e.g., bacteria, bacterial toxins, and viruses will particularly benefit from oral administration of the permeate compositions. It is expected that the gut flora from infants receiving cow's milk plus permeate will most closely mimic the gut flora from infants receiving mother's milk plus fortifier.

Other variations and embodiments of the invention described herein will now be apparent to those of ordinary skill in the art without departing from the scope of the invention or the spirit of the claims below.

What is claimed is:

1. A human nutritional supplement comprising a concentrated form of human milk permeate, said human milk permeate comprising human milk oligosaccharides filtered from human milk.

2. The human nutritional supplement of claim 1, wherein the human milk permeate is filtered from human milk pooled from two or more donors.

3. The human nutritional supplement of claim 1, further comprising vitamins and minerals.

4. The human nutritional supplement of claim 1 wherein the concentrated form of human milk permeate filtered from human milk is concentrated by reverse osmosis.

* * * * *